United States Patent [19]

Brehm et al.

[11] Patent Number: 5,433,214
[45] Date of Patent: Jul. 18, 1995

[54] INDICATOR FOR DETERMINING AND INDICATING THE FAT AND MOISTURE CONTENT OF HUMAN SKIN

[76] Inventors: Robert Brehm, Thomas-Knorr-Str. 25, D-8100 Garmisch Partenkirchen, Germany; Robert Pugh, 6 Windson Road, Kew, Richmond Surrey TWG 2EL, United Kingdom

[21] Appl. No.: 128,366

[22] Filed: Sep. 28, 1993

Related U.S. Application Data

[63] Continuation of PCT/DE93/00080, Jan. 28, 1993.

[30] Foreign Application Priority Data

Jan. 28, 1992 [DE] Germany .......... 42 02 277.0
Jan. 27, 1993 [DE] Germany .......... 43 02 218.9

[51] Int. Cl.⁶ .............................................. A61B 5/00
[52] U.S. Cl. .................................................. 128/760
[58] Field of Search ............... 128/630, 632, 749, 759, 128/760, 762; 604/303, 304, 312, 317, 318

[56] References Cited

U.S. PATENT DOCUMENTS

| | | | |
|---|---|---|---|
| 4,532,937 | 8/1985 | Miller | 128/759 |
| 4,981,145 | 1/1991 | Goldstein | 128/760 |
| 5,088,502 | 2/1992 | Miller | 128/759 |
| 5,094,248 | 3/1992 | Kawam | 128/760 |
| 5,119,828 | 6/1992 | Miller | 128/760 |

*Primary Examiner*—William E. Kamm
*Assistant Examiner*—John P. Lacyk
*Attorney, Agent, or Firm*—Herbert L. Lerner; Laurence A. Greenberg

[57] ABSTRACT

An indicator for determining and indicating the fat and moisture content of human skin includes a substrate being colored other than white. An approximately white-tinted, fat-sensitive and moisture-sensitive substance is applied to the substrate. The substance at least partially changes its color after being applied to the skin by changing its physical refractive index when brought into contact with the skin as a function of the fat and moisture content of the skin, permitting the colored substrate underneath the substance to at least partially show through and be visible. An indicator assembly for determining and indicating the fat and moisture content of human skin includes a flat face mask having locations to be measured and a plurality of the indicators being removably fastened to the locations to be measured.

14 Claims, 2 Drawing Sheets

INDICATOR FOR DETERMINING AND INDICATING THE FAT AND MOISTURE CONTENT OF HUMAN SKIN

CROSS-REFERENCE TO RELATED APPLICATION

This application is a Continuation of International Application Serial No. PCT/DE93/00080, filed Jan. 28, 1993.

BACKGROUND OF THE INVENTION

1. Field of the Invention

The invention relates to an indicator for determining and indicating the fat and moisture content of human skin, with a fat and moisture-sensitive substance applied to a substrate, which changes its color at least partially after being applied to the skin.

It is known that the skin of the face, in particular, is protected by a thin fat layer and emerging perspiration forming a coating for protection against acid. To this end, a particularly large number of sebaceous glands are present in the face, which produce fat in the form of sebaceous matter, with the sebaceous matter reaching the surface of the skin through outlet channels and providing a protection, particularly against the weather, in the form of a fatty film.

Larger sebaceous glands are located primarily in the socalled T-zone of the face, having the forehead as the crossbar and the nose down to the chin as the perpendicular portion of the T. Fatty, shiny zones can be seen there more frequently, while as a rule the cheek areas appear duller, because in that area the sebaceous glands are much smaller.

Of course, depending on the type of skin, the appearance of the skin varies or the individual facial regions are differently "greasy" because of a large sebaceous matter production, or "dry" because of a lack of water content of the uppermost skin layer. Sometimes it is hard to determine whether or not there is a lack of fat or moisture with skin which appears dry and chapped. In such a case there can always be a lack of moisture, i.e. in the fatty skin type as well as the dry skin type, while as a rule a lack of fat is only present in the dry skin type, so that in such a case a supply of moisture is required in most cases.

From a cosmetic point of view, the determination of the condition of the skin at many places and the selection of skin preparations which are suitable for the corresponding skin condition is important in that case in order to prevent damage or worsening of the skin condition.

In order to determine the skin condition it is known, for example from U.S. Pat. No. 4,532,937 to apply a thin, open-celled, microporous and hydrophobic film of a polymer material to the skin by means of an adhesive which is permeable to sebaceous matter and to leave it there for a while, in the course of which the pores of the film are filled with sebaceous matter and because of that become transparent, so that a first estimation of the sebaceous matter content is made possible in such a manner. However, the disadvantage of that method is that a reaction time of at least 30 minutes is required, and the method is not suitable for detailed studies and for the prolonged storage of the test results, because the sebaceous matter taken up in the pores has a tendency to spread rapidly over the entire film.

SUMMARY OF THE INVENTION

It is accordingly an object of the invention to provide an indicator for determining and indicating the fat and-/or moisture content of the skin, which overcomes the hereinafore-mentioned disadvantages of the heretofore-known devices of this general type and which does so in a simple manner and particularly within a very short period of time.

With the foregoing and other objects in view there is provided, in accordance with the invention, an indicator for determining and indicating the fat and moisture content of human skin, comprising a substrate being colored other than white; and an approximately white-tinted or colored, fat-sensitive and moisture-sensitive substance being applied to the substrate, the substance at least partially changing its color after being applied to the skin by changing its physical refractive index when brought into contact with the skin as a function of the fat and moisture content of the skin, permitting the colored substrate layer underneath the substance to at least partially show through and be visible.

In accordance with another feature of the invention, the substance essentially contains highly porous silicon dioxide.

Thus, a rapidly reacting, fat and moisture-sensitive substance is used with an indicator of this type which, when coming into contact with water or fat, changes its refractive index because of a purely physical reaction so that the colored substrate layer underneath it becomes visible because of this reaction.

In accordance with a further feature of the invention, the substrate has a larger area than the applied substance and extends beyond the substrate surface by the same amount on all sides.

In accordance with an added feature of the invention, the substrate is formed of paper or a plastic, and the back of the substrate can also be coated with a self-adhesive layer, which is covered by protective paper.

In accordance with an additional feature of the invention, the substance itself is imprinted on the substrate by means of known printing methods, and the thickness of the substance is 10 to 50$\mu$, in particular 20 to 30$\mu$.

There are two particularly suitable possibilities for application of the indicator.

According to one possibility, there is provided an indicator assembly in which a plurality of indicators, that are shaped the same or differently, are formed of the substrate and the substance imprinted thereon and have a respective size of approximately 5 to 10 cm$^2$, are removably applied to a planar flat face mask at the locations to be measured.

However, according to another possibility, which is particularly practical, there are provided substrate areas which are imprinted on a flexible foil, corresponding to a schematic or diagrammatic face mask, at the locations to be measured and are covered with the substance. Thus, the face mask can be printed as a whole on the face.

In accordance with another feature of the invention, the imprinted face mask is covered with a protective sheet and the face mask and the protective sheet have lateral protrusions which can be removed through a perforation and are glued to each other so as to connect the face mask and the protective sheet with each other.

In accordance with a concomitant feature of the invention, the face mask has a comparison scale for different fat and moisture contents.

Other features which are considered as characteristic for the invention are set forth in the appended claims.

Although the invention is illustrated and described herein as embodied in an indicator for determining and indicating the fat and moisture content of human skin, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
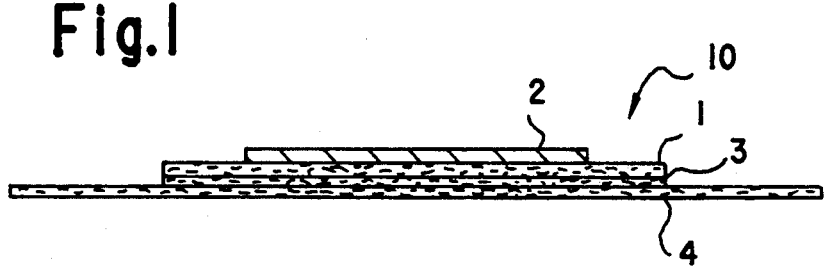
FIG. 1 is a diagrammatic, longitudinal-sectional view of a layer structure of an indicator for individual applications.

Referring now to the figures of the drawing in detail and first, particularly, to FIG. 1 thereof, there is seen a greatly enlarged section showing an indicator 10 with a small amount of a substance 2 that has been applied to a substrate 1, which may be formed of paper, PVC or polyester and which advantageously has a colored surface. The substance 2 has the property of changing its refractive index because of a color reaction when it comes into contact with moisture or fat, so that in this way the colored layer of the substrate 1 shines through to the outside. This substance 2 is advantageously applied to the substrate in a printing process by means of conventional techniques, such as offset printing, lithographic printing, roller coating or print screening, or by any other known manner.

In the instant case the substrate 1 has been coated in a screen printing process with the substance 2 at a thickness of approximately 15 to 50μ, and preferably 20 to 30μ, which is entirely sufficient for the desired effect.

When such an indicator 10 being formed of the substrate 1 and the substance 2 is to be employed individually, it is practical to also coat the back of the substrate 1 with a self-adhesive layer 3 in order to apply it first on a larger surface, or to cover it with protective paper 4 prior to its use, as will be explained below.

Figure 2:
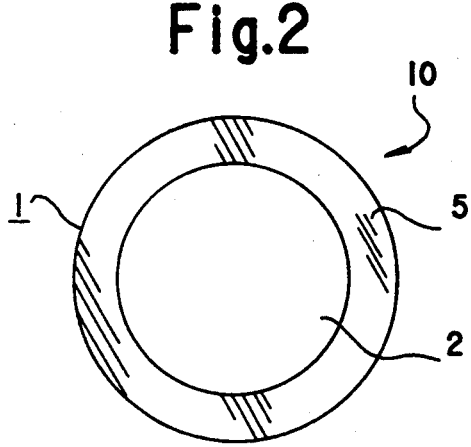
FIG. 2 is a top-plan view of an indicator in a fresh, unused state.

As is seen in FIG. 2, such an individual indicator 10 can be manufactured, for example, in the shape of a round disk or it can be stamped out later, with the substrate 1 advantageously extending beyond the diameter of the actual substance layer 2 and in this way forming an uncoated edge 5. In order to obtain a good contrast, the substrate 1 can be colored or printed blue, for example, while the substance 2 is advantageously white.

Figure 3:
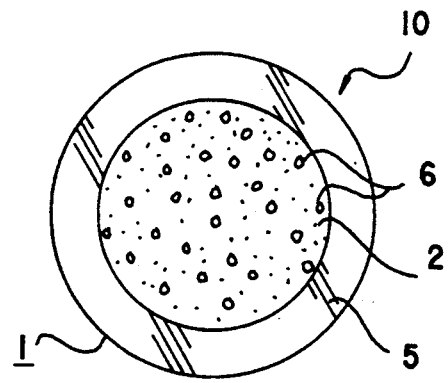
FIG. 3 is a top-plan view of such an indicator after removal from respective areas of the skin.

Then such an indicator 10 is pressed with the substance side 2 on the appropriate skin area and can be removed again after 15 seconds. In the course of this operation and in accordance with FIG. 3, appropriate areas 6 of the substance 2, which have come into contact with especially fat-containing areas or with sebaceous glands, have changed their refractive index in such a way that the originally white substance 2 has become transparent in these areas, and in this way the blue background of the substrate 1 has become visible. Depending on the size and number of these transparent areas 6 and of the colored appearance, it is possible to come to conclusions regarding high or low fat content or moisture content of the skin.

Although it is, of course, also possible to color the layer of the substance 2 in a light tone, in the course of such a step it must be assured that the refractive index of the substance does not change or become reduced too greatly by the addition of respective color pigments.

Figure 4:
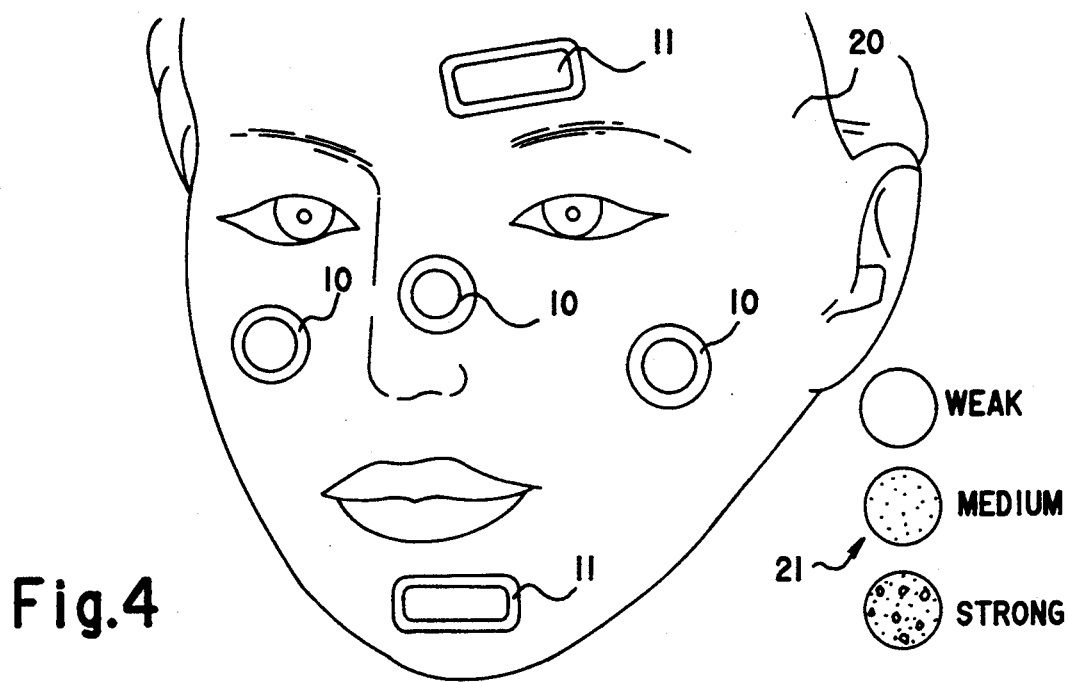
FIG. 4 is a perspective view of a face mask with glued-on indicators and a comparison scale.

A possible application for making the determination of the skin properties easier is shown in FIG. 4. In this case, appropriate indicators have already been glued to a diagrammatically illustrated face mask 20 at those places which are advantageously employed for assessing the condition of the skin. Namely, for example, round indicators 10 are placed on the cheeks and on the nose and rectangular indicators 11 are placed in the area of the forehead and the chin. In order to determine the fat and moisture content of the skin, these indicators 10 or 11, which are glued to the mask, are removed from the mask 20, pressed on the appropriate skin areas of the face and subsequently glued back on the mask after the above-described short reaction time of approximately 15 seconds. Through the use of a scale 21 provided on the side of the mask, it is then directly possible to come to conclusions regarding the fat content of the skin by a comparison of the indicators which were glued back on. In this case the discoloration of the originally white substance 2 is greater for fatter skin, so that it is possible to start appropriate countermeasures or to select appropriate preparations.

Figure 5:
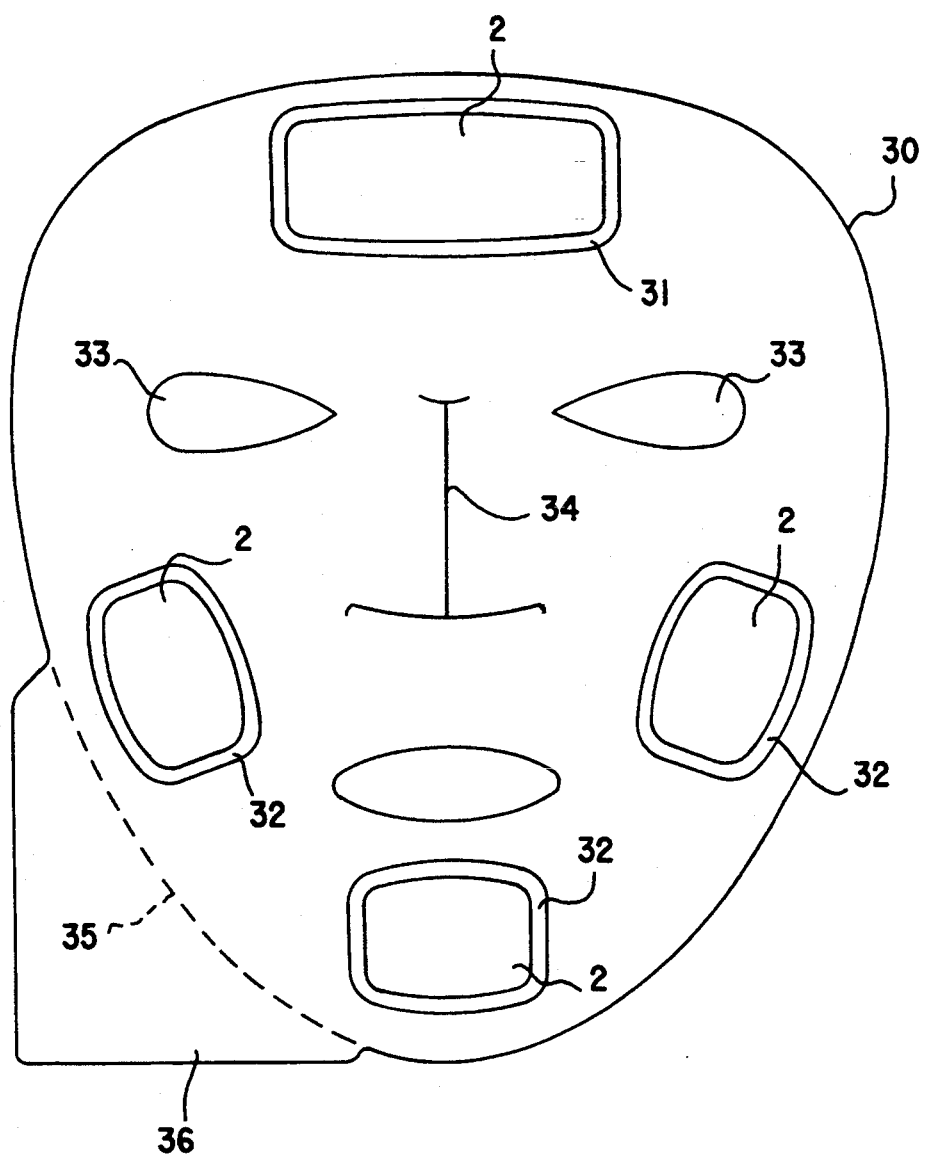
FIG. 5 is a front-elevational view of a flexible face mask with an imprinted substrate area which is covered by a substance.

A further possibility of use is illustrated in FIG. 5. In this case, substrate areas 31 or 32 of smaller size, which have been covered with the appropriate substance 2, have already been pressed on areas to be measured on a diagrammatically illustrated face mask 30 formed of paper or a flexible foil. In addition, this mask 30 has cutouts 33 for the eyes and impressed slits 34 for the nose, so that it is then possible to press this mask 30 directly on the face where it remains for a while. It is then possible to determine the respective discolorations of the substance 2 after its removal and to compare them with a scale.

It is practical for easier manipulation to cover this mask 30 with a non-illustrated cover sheet, which has the same outer contours. For this purpose, the face mask 30 and the cover sheet advantageously have lateral projections 36 which can be removed through the use of a perforation 35 and which are glued to each other, so that the cover sheet and the mask 30 are connected with each other in this way. For use, the lateral projection or protruding corner 36 is removed so that the mask 30 alone can be manipulated and pressed on the face.

Thus, the result of the foregoing is an indicator, by means of which it is possible to determine the fat and/or moisture content of the skin in a rapid and simple manner.

We claim:

1. An indicator for determining and indicating the fat and moisture content of human skin, comprising:

a substrate being colored other than white; and
approximately white-tinted, fat-sensitive and moisture-sensitive, highly porous silicon dioxide applied to said substrate, said silicon dioxide changing its physical refractive index when brought into contact with the skin as a function of the fat and moisture content of the skin, such that the colored substrate underneath said silicon dioxide shows through at least partially and becomes visible.

2. The indicator according to claim 1, wherein said substrate has a surface being larger than said silicon dioxide applied thereon and extends beyond the surface of said silicon dioxide by the same width all around.

3. The indicator according to claim 1, wherein said substrate is formed of a material selected from the group consisting of paper and plastic.

4. The indicator according to claim 2, wherein said substrate has a back surface, and including a self-adhesive layer coating said back surface, and a protective paper covering said coating.

5. The indicator according to claim 1, wherein said silicon diozide is printed on said substrate.

6. The indicator according to claim 5, wherein said silicon dioxide has a layer thickness of from 15 to 50$\mu$.

7. The indicator according to claim 5, wherein said silicon dioxide has a layer thickness of from 20 to 30$\mu$.

8. The indicator according to claim 1, wherein said substrate and said silicon dioxide printed on said substrate have a size of approximately from 5 to 10 $cm^2$.

9. An indicator assembly for determining and indicating the fat and moisture content of human skin, comprising:
a flat face mask having locations to be measured; and
a plurality of indicators being removably fastened to said locations to be measured, each of said indicators having:
a substrate being colored other than white; and an approximately white-tinted, fat-sensitive and moisture-sensitive substance being applied to said substrate, said substance at least partially changing its color after being applied to the skin by changing its physical refractive index when brought into contact with the skin as a function of the fat and moisture content of the skin, permitting the colored substrate underneath said substance to at least partially show through and be visible.

10. The indicator assembly according to claim 9, wherein said substance is printed on said substrate, and said substrate and said substance printed on said substrate have a size of approximately from 5 to 10 $cm^2$.

11. The indicator assembly according to claim 9, including a flexible foil corresponding to said face mask, said indicators being printed on said flexible foil at said locations to be measured.

12. The indicator assembly according to claim 11, including a protective sheet covering said printed face mask.

13. The indicator assembly according to claim 12, wherein said face mask and said protective sheet have lateral protrusions to be separated with a perforation and are glued together.

14. The indicator assembly according to claim 9, wherein said face mask has a comparison scale for different fat and moisture contents.

* * * * *